United States Patent [19]

Rosner

[11] 4,339,618

[45] Jul. 13, 1982

[54] PROCESS FOR THE PRODUCTION OF SUBSTITUTED NITROARYL COMPOUNDS

[75] Inventor: Manfred Rosner, Muttenz, Switzerland

[73] Assignee: Ciba-Geigy AG, Basel, Switzerland

[21] Appl. No.: 160,254

[22] Filed: Jun. 17, 1980

[30] Foreign Application Priority Data

| | | | |
|---|---|---|---|
| Jun. 21, 1979 | [CH] | Switzerland | 5806/79 |
| Sep. 4, 1979 | [CH] | Switzerland | 7980/79 |
| Apr. 9, 1980 | [CH] | Switzerland | 2716/80 |
| Apr. 9, 1980 | [CH] | Switzerland | 2717/80 |

[51] Int. Cl.$^3$ .................. C07C 76/02; C07B 11/00; C07C 79/12; C07C 79/10; C07C 79/46

[52] U.S. Cl. .................. 568/937; 260/465 B; 260/688; 568/938; 568/939; 568/940; 564/218; 564/223

[58] Field of Search .............. 568/932, 933, 934, 935, 568/936, 937, 938, 939, 940; 260/688

[56] References Cited

U.S. PATENT DOCUMENTS

| | | | |
|---|---|---|---|
| 2,435,544 | 2/1948 | Kokatnur | 568/935 |
| 2,810,000 | 10/1957 | Schenck | 568/937 |
| 3,086,062 | 4/1963 | Oltay | 568/932 |
| 3,100,797 | 8/1963 | Harris et al. | 260/688 |
| 3,183,275 | 5/1965 | Sparks | 568/937 |
| 3,822,251 | 7/1974 | Vrolyk et al. | 568/935 |
| 3,927,127 | 12/1975 | Damiano | 568/933 |
| 3,981,933 | 9/1976 | Cook et al. | 568/931 |
| 4,036,838 | 7/1977 | Vogel et al. | 568/932 |

FOREIGN PATENT DOCUMENTS

| | | | |
|---|---|---|---|
| 55-33406 | 3/1980 | Japan | 568/934 |
| 1436954 | 5/1976 | United Kingdom | 260/688 |

OTHER PUBLICATIONS

C.A., vol. 84, 104, 690a (1976).

*Primary Examiner*—Teddy S. Gron
*Attorney, Agent, or Firm*—Sprung, Horn, Kramer & Woods

[57] ABSTRACT

The invention relates to a process for the production of nitroaryl compounds which are at least monosubstituted, by nitration of aryl compounds which are at least monosubstituted, which process comprises carrying out the nitration in a two-phase system which consists of an inorganic phase consisting of sulfuric acid having a concentration of at least 80% and an organic phase consisting of an inert organic liquid in which the nitration product is almost insoluble in the presence of sulfuric acid, at a temperature in the range from −30° to 100° C., with nitric acid as nitrating agent.

The novel process can be generally employed for aryl compounds which are at least monosubstituted. The corresponding nitroaryl compounds are obtained in high yield and isomeric purity.

10 Claims, No Drawings

PROCESS FOR THE PRODUCTION OF SUBSTITUTED NITROARYL COMPOUNDS

The invention relates to a process for the production of nitroaryl compounds which are at least monosubstituted, by nitration of aryl compounds which are at least monosubstituted.

Nitration reactions and nitrated monosubstituted aryl compounds have attained considerable importance in the art. The nitration processes are designated individually and batchwise, depending on the particular requirements regarding the purity of the products, in respect of the degree of nitration and isomer purity, as frequently the reaction temperature is critical and must not exceed specific values; and, on the other hand, the concentration of the acid to be used and the reaction medium are also of decisive importance.

In the wake of the simplification of process technologies relating to a more general use of apparatus and, in particular, of a procedure which is more advantageous ecologically, there is therefore a genuine need in the art for processes in which several products can be obtained by one and the same procedure. Furthermore, continuous processes are economically superior to the batch processes. Accordingly it is the object of the present invention to provide a process which does not have the disadvantages of the processes designed to suit each individual mode of operation for the nitration of aryl compounds which are at least monosubstituted.

This object is achieved by the process of this invention. Surprisingly, it has been found that, if the nitration is carried out in a reaction medium which consists of two liquid phases, one of said phases being an organic phase consisting of an inert organic liquid, i.e. one which does not participate in the reaction, and in which the nitration product in the presence of concentrated sulfuric acid is virtually insoluble, and the other being an inorganic phase consisting of at least 80% sulfuric acid, in the temperature range from −30° to 100° C., with nitric acid as the nitrating agent, the corresponding nitroaryl compounds are obtained in high yield by a simple and ecologically advantageous process which can be used quite generally for aryl compounds which are at least monosubstituted.

A low saturation solubility of the reaction product in the organic phase is certainly permissible, as the phase is recycled and thus neither a further concentration nor a loss of product takes place.

A further special feature of the process of this invention is that the inorganic phase can often have the effect of extracting the nitro compound from the organic phase. For this reason, it is even possible also to use those organic liquids in which the reaction product usually is more or less soluble, but in which the solubility of the product decreases sharply in the presence of sulfuric acid.

Specifically, the particular reaction conditions are also of importance as regards the possibilities of using inert liquid and nitration substrate.

Thus, under milder nitration conditions, for example in the temperature range from −10° to 30° C. and using a sulfuric acid concentration in the inorganic phase of about 90%, chlorobenzenes are still excellent inert liquids during the nitration. If, on the other hand, the nitration conditions are severe, for example a temperature of 50° C. or above and sulfuric acid monohydrate as the inorganic phase, the chlorobenzenes previously employed as an inert liquid can also be nitrated by the novel process, with the proviso that the principle of phase separation of the nitration product between the inorganic phase and the organic inert phase is retained. In the latter case, of course, the organic inert liquids employed must be those which remain inert to the reaction despite the severe nitration conditions. Such liquids are the petroleum distillates of various boiling ranges, in particular of the boiling ranges between 130° and 200° C.

Aryl compounds which are at least monosubstituted and which are suitable for nitration by the process of this invention are, for example, those which contain an alkoxy group, but in particular those which contain electronegative substituents, such as a carboxyl group, acylamido group, a cyano group, or a halogen such as bromine or, in particular, chlorine.

Examples of such compounds are: benzoic acid, o- and p-chlorobenzoic acid, acetylaniline, 4-acetamido-1-methoxybenzene, 4-propionamido-1-methoxybenzene, 4-cyanoacetanilide, 4-methoxyacetanilide, 4-methoxyethoxyaniline, 2,5-dichloroacetanilide, 2,5-dibromoacetanilide, 2,6-dichloropropionanilide, 2,4-dichlorobenzene, 2,6-diiodoaniline, 2-chloroaniline and 4-dimethylaminotoluene.

Suitable organic liquids which are inert under the reaction conditions and which can be used for the novel process are, in particular, non-polar organic solvents, for example aliphatic and aromatic chlorinated hydrocarbons, aliphatic hydrocarbons and others, for example chlorobenzene or o-dichlorobenzene, and also tetrachloroethane, but especially petroleum distillates of various boiling ranges, for example white spirit, naphtha and the like. The individual liquid hydrocarbons can, of course, also be employed in pure form, for example in the form of n-octane, n-heptane and the like.

However, it is also possible to use other organic solvents if these satisfy the defined parameters.

The amount of inert organic solvent can vary within wide limits and is required, in particular, for better stirrability and heat removal. As, however, some 95% of solvent is recovered again and can be reused without further working up, the quantity only has a certain importance with regard to the production capacity.

An advantageous ratio of solvent to substrate is from 3:1 to 8:1.

The sulfuric acid to be used as the inorganic phase in the practice of this invention can consist of 100% $H_2SO_4$, i.e. the so-called monohydrate ($SO_3.H_2O$), but it can also contain a relatively small amount of water. Concentrated sulfuric acid of commercial quality, which usually contains 96% of $H_2SO_4$ and 4% of water, can be used. However, the acid can also contain up to 10% of sulfur trioxide, based on the monohydrate. The sulfuric acid should, however, have a $H_2SO_4$ concentration of at least 80%. For a wide variety of practical applications, the range of 90 to 95% $H_2SO_4$ is the most advantageous.

The amount of sulfuric acid, calculated as $H_2SO_4$, should preferably be between 500 and 1000 percent by weight, based on the reaction substrate. In many cases, however, a smaller amount, for example 300%, also suffices.

The nitric acid used for the nitration should have a strength which corresponds to conventional concentrated (c. 64%) nitric acid. The nitration is advantageously carried out with a mixture of nitric acid and sulfuric acid, i.e. nitrating acid, but can also be carried out with nitric acid alone.

The weight ratio of sulfuric acid monohydrate to concentrated nitric acid in the nitrating acid is about 1:1.

Preferably, the nitric acid concentration in this nitrating acid is adjusted such that the amount of nitric acid present is slightly in excess of the amount theoretically required for mononitration. The excess is usually about 5%. It is also possible to use concentrated nitric acid on its own as nitrating agent, as sulfuric acid is in any case present as the reaction medium. The amount of sulfuric acid monohydrate employed must then, however, be correspondingly increased, as otherwise the remaining acid mixture acts as an acid of low concentration with which poorer yields and, possibly, less advantageous isomer ratios in respect of the desired isomer might be obtained.

Irrespective of the fact that the process of the invention can also be carried out batchwise, it is especially suitable for continuous operation.

The reaction substrate in sulfuric acid is charged into a storage flask and dissolved or emulsified by heating to about 60° C. The mixture is then cooled to 20°–25° C. without the reaction substrate precipitating. The inert solvent is kept ready in a second flask, cooled to the desired temperature beforehand, and mixed either with the sulfuric acid solution or fed direct to the reactor. A third flask is charged with the nitrating acid.

In accordance with the desired rates of flow, the reaction components and the organic inert liquid are charged continuously into a reactor from the individual storage flasks. The nitration reaction takes place in the desired period of time and temperature range in this reactor, in accordance with the dimensions of the reactor and the auxiliary apparatus.

When the reaction is complete, the entire reaction mixture is fed into a phase separating vessel, in which the inert organic liquid phase is separated and recycled to the reaction. The inorganic phase of the crude nitration product can be further worked up as in the batchwise method. However, this working up step can be adapted in respect of the apparatus and time such that a completely continuous operation is ensured.

In the batchwise procedure, the organic inert liquid is usually introduced initially in an amount which is about 3 to 8 times that of the reaction substrate employed. The reaction substrate is then put into the reactor, and 85–100% sulfuric acid is then added in an amount which is about six times that of the reaction substrate. The reaction substrate is dissolved or suspended by the sulfuric acid in this phase.

The temperature is then adjusted to the reaction temperaure and the nitrating acid, which is in an amount about 5% above the stoichiometric amount necessary for mononitration of the reaction substrates employed, is then run in, while keeping the temperature in the same range.

The reaction mixture is then further stirred, so that it can react further, and phase separation then takes place. The inorganic phase is run into the cold water and is diluted only to the extent necessary to precipitate the product.

It frequently suffices to lower the concentration of the sulfuric acid to 60–80%, in which case the filtrate acid can be recycled by increasing the concentration with $SO_3$ and re-used in the same process. The product is collected by filtration, washed with water, and dried if desired.

The process of the invention does not, of course, preclude a procedure at temperatures above 50° C. to 100° C., by which means even substances which are more difficult to nitrate can be nitrated. This is possible in particular because of the advantageous removal of heat and the short sojourn times in the continuous process.

However, because of the products which it is desired to obtain and their sensitivity to the formation of by-products, the nitration is in particular carried out at low temperature in the range from −10° to 50° C.

When the reaction is carried out discontinuously, the nitration is preferably carried out in the temperature range from 10° to 35° C.

When the reaction is carried out continuously, the nitration is carried out advantageously over the range from −10° to 100° C.

The continuous variant of the novel process firstly enables the reaction to proceed within a very short period and so to counteract the formation of by-products caused by over-nitration or sulfonation; and, secondly, because of the rapid removal of the heat of reaction, no sudden changes in temperature arise, which makes the process much more reliable in operation and, of course, less hazardous.

However, as regards the individual substrates to be nitrated, the novel process also offers e.g. the following advantages:

(a) Under the conditions of the two-phase process virtually no further sulfonation takes place and, accordingly, higher yields are obtained.

(b) The modified reaction conditions permit the nitration to be carried out at elevated temperature without the occurrence of secondary reactions, and thereby facilitating the removal of heat. A change-over from expensive dry ice to brine as the coolant medium is possible.

(c) As a result of the substantially better heat removal, it is possible to carry out the reaction more rapidly. This can be expressed in better space-time yields.

(d) Substantial savings in energy result because the cooling or heating requirements are lower than those of former processes.

(e) Ecological advantages accrue from the saving in working-up procedures and the re-use of the organic inert liquid.

(f) Because of the more advantageous time/temperature relationships, the process is most suitable for a continuous procedure.

The compounds obtained by the novel process can be valuable dyestuff intermediates which e.g. after reduction of the nitro group to the amino group can be used as coupling components for the preparation of azo dyes or azo pigments or as diazo components in the preparation of azo dyes. However, the compounds themselves are also chemicals which can be used in various fields of chemistry.

The following Examples illustrate the novel process without restrictng it to what is described therein.

EXAMPLE 1

Batchwise nitration of benzoic acid 500 g (about 700 ml) of petroleum distillate with a boiling point of 110° to 140° C. are initially introduced into a 1.5 liter flask with a bottom outlet. With stirring, 122.1 g of 100% benzoic acid are introduced, and 732 g of 98% sulfuric acid are added. The resultant suspension is then warmed to about 55° C. and stirred until the benzoic acid has dissolved in the sulfuric acid to give a pale yellow solution (duration about 10 minutes). The two-phase mixture is then cooled again to 20°–25° C., without the benzoic acid crystallising out during this operation. Then 131.3 g of 50.4% nitrating acid are introduced and a maximum temperature of 20° to 25° C. is kept by means of a cooling bath. Depending on the cooling, the time taken for the addition of nitrating acid is about 30 to 40 minutes. When the addition of the acid is complete, the resultant mixture is stirred for a further 30 minutes. Total volume: about 1300 ml, of which the upper phase (petroleum) consists of about 700 ml and is colourless, and the lower phase (reaction mass) consists of about 600 ml and is yellowish brown.

About 1.8 l of cold water are then put into a 4 liter glass beaker and, with stirring, the lower phase of the reaction mixture is introduced in the course of about 20 to 30 minutes. The temperature in the glass beaker rises to 55° to 60° C. during this addition. The temperature is kept constant within this range by adding water or ice. The final volume is then bulked to 3 liters and the resultant mixture is stirred for a further 30 minutes at 55° to 60° C.

The beige-coloured suspension is cooled to 40° C. by means of an ice-bath and is stirred for a further 30 minutes to obtain a steady state. Filtration is carried out at the same temperature of 40° C. through a 16 cm $\phi$ suction filter. The product is washed with about 1 liter of cold water in portions. Towards the end of washing, the filtrate has a pH value of about 2.5 to 2.6.

The filtration time is about 30 seconds and the washing time about 45 seconds.

The product is dried at 70° to 80° C. in a water-jet vacuum, affording m-nitrobenzoic acid with a melting point of 140° C. (literature data 140° to 141° C.).

According to LC analysis, the product is 98.5 to 99.5% pure. Yield: about 128 g of approximately 99% pure product, (according to LC)=about 127 g of 100% pure product, which corresponds to 76% of theory.

An amount of about 490 g of petroleum spirit remains in the separating flask; this is about 98% of the amount originally used and can be re-used for the next batch.

EXAMPLE 2

Nitration of benzoic acid—continuous

A storage flask is charged with 112.1 g of benzoic acid in 732 g of 98% $H_2SO_4$ and the mixture is dissolved by heating to about 60° C. A temperature of 20°–25° C. is then established by subsequent cooling, without the benzoic acid precipitating. A second flask is charged with 700 ml of petroleum distillate as inert solvent, which is cooled to 15°–20° C. and either mixed with the sulfuric acid solution or fed direct to the reactor. A third flask is charged with 131.3 g of 50.5% nitrating acid. In accordance with their concentrations in the flasks, the components are then passed continuously through the reactor in the stoichiometric ratio previously mentioned. If desired, the petroleum spirit is fed to the reactor separately if it has not been put into the storage flask initially together with the $H_2SO_4$. The reactor is cooled with brine. The addition of the reaction substrates is controlled such that the temperature of the exiting reaction mixture is 20°–25° C.

The reaction mixture is subsequently collected in a phase separator, whereupon the petroleum phase separates from the inorganic product phase. While the upper petroleum phase is recycled for use in a subsequent batch, the lower phase is poured into ice-water and worked up as in Example 1. Results almost identical with those of Example 1 are obtained.

EXAMPLE 3

Nitration of 2,5-dichloroacetanilide—continuous

A storage flask is charged with 750 ml of petroleum spirit (boiling range: 110°–140° C.) and 204 g of 2,5-dichloroacetanilide in 1265 g of 98% sulfuric acid. A second storage flask is charged with 130.7 g of 50.6% nitrating acid. As in Example 2, the reaction components are passed through the cooled reactor and the desired exit temperature is adjusted to 20°–25° C. by controlling the rate of flow. The rate of flow of nitrating acid is 10 ml/min., and that 2,5-dichloroacetanilide in the two-phase system is about 165 ml/min. The experiment is complete after about 10 minutes.

The resultant 2,5-dichloro-4-nitroacetanilide solution in the inorganic phase, which is decanted from the phase separator, is poured into ice-water and the product is worked up as in Example 1. The yield of 2,5-dichloro-4-nitroacetanilide is 85% of theory.

EXAMPLE 4

Batchwise nitration of 2,5-dichloroacetanilide

A 2.5 liter flask is charged with 550 g of petroleum distillate (boiling range: 110°–140° C.). With stirring, 162.0 g of 100% 2,5-dichloroaniline are then added and the mixture is warmed to 45° C., whereupon a solution forms. The 108 g of 100% acetic anhydride are added dropwise in the course of about 15 minutes and the temperature is allowed to rise to 65° C. After the reaction mixture has been stirred for 15 minutes at 65° C., the addition of 1265 g of 98% sulfuric acid is commenced, while ensuring that the temperature does not rise substantially above 70°–75° C. After addition of about 20–25% of the sulfuric acid, the precipitated acetanilide starts to dissolve. Hardly any further exothermic reaction ensues when the remainder of the sulfuric acid is added, and the temperature falls to about 60° C. The temperature of the 2-phase mixture is brought to 20°–25° C. by further cooling, and the feed of 128.2 g of 50.2% nitrating acid is commenced immediately at a temperature not higher than 25° C. The addition is complete after about 50 minutes and the reaction mixture is stirred for a further 20 minutes at 20° to 25° C.

The reaction mixture is then charged into a 2 liter separating funnel, whereupon a lower, dark-brown layer separates immediately. The upper, petroleum layer is largely colourless or only a pale yellow colour. The lower layer is then passed slowly into a glass beaker, into which water of 40° C. is stirred. The temperature is kept at a maximum of 50° C. by the constant addition of altogether about 1300 g of ice (duration c. 30 minutes). A brownish yellow suspension is finally obtained. The suspension is stirred for a few minutes at 50°–55° C. and then filtered. The filter cake is washed with 1.5 liters of cold water. If the filtrate is still not neutral, the filter cake is washed once more, pressed well and, if desired, dried. Mother liquor and wash water are combined. The amount of petroleum spirit remaining in the separating funnel is 535 g and, after replenishment to the original amount, can be re-used in the next batch. Yield: c. 235 g of 2,5-dichloro-4-nitroacetanilide. The product is sufficiently pure for it to be used direct in dye or pigment manufacture.

EXAMPLE 5

Batchwise nitration of 4-methoxyacetanilide

A 2.5 liter flask is charged with 800 g of chlorobenzene. With stirring, 123.2 g of 100% p-anisidine (preferably as melt) are then added. Then 102 g of acetic anhydride are added dropwise in the course of about 15 minutes, whereupon the temperature rises to 65° C. After stirring for 15 minutes at 65° C., the mixture is cooled to about 30° C. within about 10 minutes using a cooling bath, whereupon beige-coloured crystals of the acetanisidide begin to precipitate in the temperature range from about 45° C. The resultant suspension is slightly viscous, but readily stirrable. The addition of 800 g of 92% sulfuric acid is then commenced, with care being taken that the temperature does not much exceed 30°–40° C. The addition takes about 10 minutes. With further cooling, the addition of 101.2 g of 62.3% $HNO_3$ is commenced immediately at a maximum temperature of 25° C. During the addition, the temperature can be allowed to rise to 20°–25° C. With the first few drops of $HNO_3$ the emulsion starts becoming fluid immediately and the original blue colour changes to brown. The addition is complete after about 10 minutes and the batch is stirred for 20 minutes at 20° to 25° C. until the reaction is complete. Volume of the solution: about 1450 ml. The reaction mixture is then charged into a 2 liter separating funnel, whereupon a lower, dark-brown layer separates immediately. The upper, chlorobenzene layer is largely colourless or only a pale yellow colour. The lower layer is then passed slowly into a glass beaker, into which a mixture of 300 g of ice and water is stirred. The temperature is kept at around +5° C. by the constant addition of altogether about 1500 g of ice (duration c. 30 minutes). A thick yellow suspension is finally obtained. The suspension is stirred and then filtered. The filter cake is washed with 350 ml of ice-water, well pressed and, if desired, dried. Mother liquor and wash water are combined. The amount of chlorobenzene remaining in the separating funnel is about 760 g and, after replenishment to the original amount, can be re-used in the next batch. Yield: about 193 to 195 g of 4-acetamido-2-nitro-anisole in 99% purity. Melting point: about 150°–151° C.

The product obtained by this method is sufficiently pure to be reacted in a subsequent synthesis step to give 3-benzylamino-4-methoxyacetanilide.

EXAMPLE 6

Continuous process

A storage flask is charged with 400 g of petroleum distillate with a boiling range of 110°–140° C. and 123.2 g of p-anisidine (preferably as melt). The resultant solution is acylated by gradually running in 130.1 g of propionic anhydride, in the course of which the temperature may rise to about 70° C. The solution is then advantageously cooled to room temperature and then 800 g of 95% sulfuric acid are added. The addition of $H_2SO_4$ can be made both discontinuously in a cooled vessel and continuously in a reactor equipped with a heat exchanger. The temperature during the addition should not rise much above 30°–35° C. The heterogeneous reaction mixture is then passed continuously through a reactor cooled with brine (e.g. flow pipe) and into which 102 g of 62.3% nitric acid (based on the content of acetanilide) are added continuously. The rate of flow through the reactor is adjusted to the cooling capacity such that the nitration mixture which exits has a temperature of 20°–25° C. The reaction mixture (total volume: 1250 ml) is collected in a separator, whereupon two phases again separate. The upper petroleum phase is almost colourless and continuously decanted. It can be re-used without processing (amount recovered: about 390 g). The lower, inorganic phase is poured continuously into 2 liters of a mixture of water and ice, whereupon the product precipitates in the form of yellow crystals. The precipitate is washed and dried, affording c. 215 g (c. 92% of theory) of 2-nitro-4-propionamido-anisole with a melting point of c. 105° C. Purity: c. 96–97%.

I claim:

1. A process for the production of mono-nitro-substituted aryl compounds which are otherwise at least monosubstituted with an electronegative substitutent, by mono-nitration of aryl compounds which are at least so monosubstituted, which process comprises carrying out the nitration by adding nitric acid to a two-phase system which consists of an inorganic phase consisting of sulfuric acid having a concentration of at least 80% and an organic phase consisting of an inert organic liquid in which the nitration product is almost insoluble in the presence of sulfuric acid, at a temperature in the range from −30° to 100° C., with nitric acid or a mixture of nitric acid and sulfuric acid as nitrating agent.

2. A process according to claim 1, wherein the inert organic liquid is a nonpolar organic solvent.

3. A process according to claim 1, wherein the inert organic liquid is an aliphatic or aromatic chlorinated hydrocarbon, or an aliphatic hydrocarbon.

4. A process according to claim 3, wherein the inert organic liquid is chlorobenzene, o-dichlorobenzene, tetrachloroethane, or a petroleum distillate of boiling range between 130° and 200° C.

5. A process according to claim 4, wherein the inert organic liquid is white spirit or naphtha.

6. A process according to claim 1, wherein the inorganic phase is sulfuric acid having a concentration of 85 to 100%.

7. A process according to claim 1, wherein the sulfuric acid, calculated as $H_2SO_4$, is employed in an amount of 300 to 1000% by weight, based on the amount of the reaction substrate.

8. A process according to claim 1, wherein the nitration is carried out with a mixture of concentrated sulfuric acid (monohydrate) and concentrated nitric acid in the weight ratio of 1:1.

9. A process according to claim 1, wherein the nitration is carried out continuously.

10. A process according to claims 1 or 9, wherein the nitration is carried out continuously at a temperature in the range from −10° to 100° C., and batchwise at a temperature in the range from 10° and 35° C.

* * * * *